US00PP20829P3

(12) United States Plant Patent

Álamo et al.

(10) Patent No.: US PP20,829 P3

(45) Date of Patent: Mar. 16, 2010

(54) BLUEBERRY PLANT NAMED 'DOLORES'

(50) Latin Name: *Vaccinium corymbosum L.*
Varietal Denomination: cv. Dolores

(75) Inventors: Antonio Abad Álamo, Huelva (ES); José Ulf Hayler López, Huelva (ES); Paul M. Lyrene, Micanopy, FL (US)

(73) Assignee: Royal Berries S.L., Almonte (ES)

( * ) Notice: Subject to any disclaimer, the term of this patent is extended or adjusted under 35 U.S.C. 154(b) by 0 days.

(21) Appl. No.: 12/219,299

(22) Filed: Jul. 18, 2008

(65) Prior Publication Data

US 2009/0210975 P1 Aug. 20, 2009

(30) Foreign Application Priority Data

Feb. 14, 2008 (EP) ..... 20080342

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers early and forms fruit that ripens early. Attractive large dark blue crisp berries are formed which exhibit a very sweet flavor. The plant is self-fertile, and displays a generally round growth habit with evergreen foliage. No cross pollination is required. A low chilling requirement is also exhibited. No special sensitivity to common blueberry diseases has been encountered during observations to date.

6 Drawing Sheets

Botanical/commercial classification: *Vaccinium corymbosum* L./Blueberry Plant.

Varietal denomination: cv. Dolores.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 97-45' cultivar (non-patented in the United States). The male parent (i.e., pollen parent) was the 'FL 95-70' cultivar (non-patented in the United States). The parentage of the new cultivar can be summarized as follows:

'FL 97-45'×'FL 95-70'.

The seeds resulting from the pollination were shipped to Almonte, Huelva, Spain, where they sown during approximately 1998, small plants were obtained which were physically and biologically different from each other and selective research of the progeny was carried out. Selective study during spring 2002 resulted in the identification of a single plant of the new cultivar. Initially the plant was designated S02-26-03.

It was found that the new Blueberry plant of the present invention displays the following combination of characteristics:

(a) flowers early and forms fruit that ripens early,
(b) displays a generally round growth habit with attractive evergreen foliage,
(c) is self-fertile,
(d) displays a low chilling requirement, and
(e) forms in abundance attractive large dark blue crisp berries that exhibit a very sweet flavor.

The new cultivar well meets the needs of the horticultural industry and can be grown to advantage for the commercial production of blueberries.

The new cultivar of the present invention can be distinguished from all other Blueberry cultivars known to its originators. Each parent plant is unreleased to the public and accordingly is not available to the public for use as a comparative cultivar. Also, each parent plant is extinct and accordingly no longer exists for further comparative purposes by the inventors. Information presently available to the inventors indicates that the mature fruit color of the 'FL97-45' female parent was very dark unlike the light blue fruit coloration of the new cultivar. Also, available information indicates the fruit of the 'FL95-70' male parent was considerably less firm than that of the new cultivar and the fruit coloration of the 'FL95-70' cultivar was often poor with the display of some reddish or greenish-white coloration when fully ripe, unlike that of the new cultivar. When compared to the 'Sharpblue' cultivar (non-patented in the United States), the new cultivar retains its leaves during the winter at Almonte, Huelva, Spain unlike the 'Sharpblue' cultivar. When compared to the 'O'Neal' cultivar (non-patented in the United States), the 'O'Neal' cultivar is partially defoliated during the winter unlike the new cultivar. When compared to the 'Star' cultivar (U.S. Plant Pat. No. 10,675), the growth habit of the new cultivar tends to be rounded and less upright, the flowers of the new cultivar tend to be more susceptible to Botrytis, and the new cultivar produces fruit approximately two weeks earlier at Almonte, Huelva, Spain. When compared to the 'Millenia' cultivar (U.S. Plant Pat. No. 12,816) the new cultivar is self-fertile unlike the 'Millenia' cultivar. When compared to the 'Misty' cultivar (non-patented in the United States), the new cultivar forms darker blue berries.

The new cultivar was first asexually reproduced by the rooting of softwood cuttings during the summer of 2002 at Almonte, Huelva, Spain. Such asexual propagation has shown that the characteristics of the new cultivar are firmly fixed and are stably transmitted from one generation to another. Accordingly, the new cultivar asexually reproduces in a true-to-type manner.

The new cultivar has been named 'Dolores'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings were approximately five years of age, and were being grown outdoors at Almonte, Huelva, Spain.

DETAILED DESCRIPTION

Figure 1:
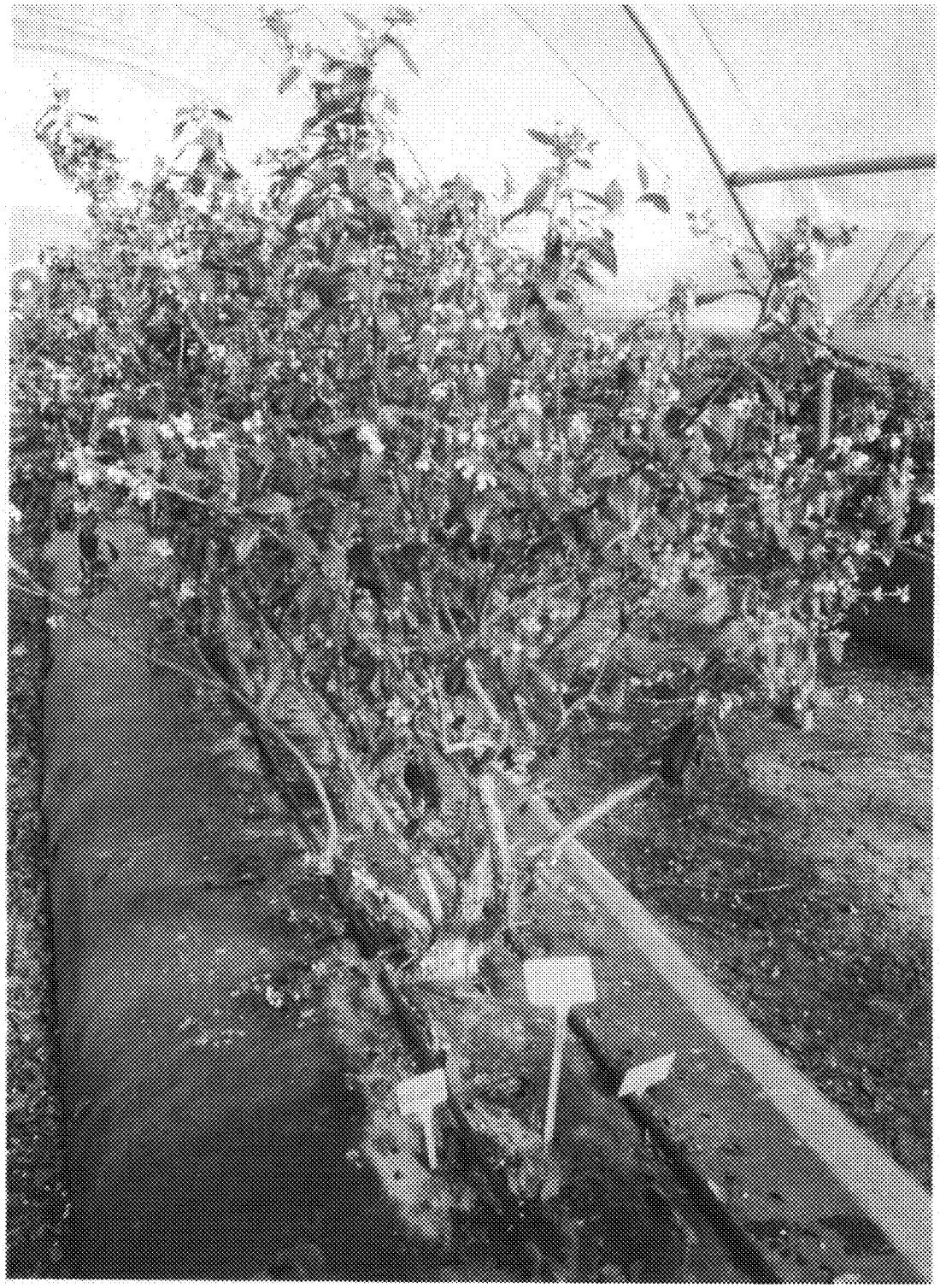
FIG. 1 shows an overall view of a typical flowering plant of the new cultivar.
Figure 2:
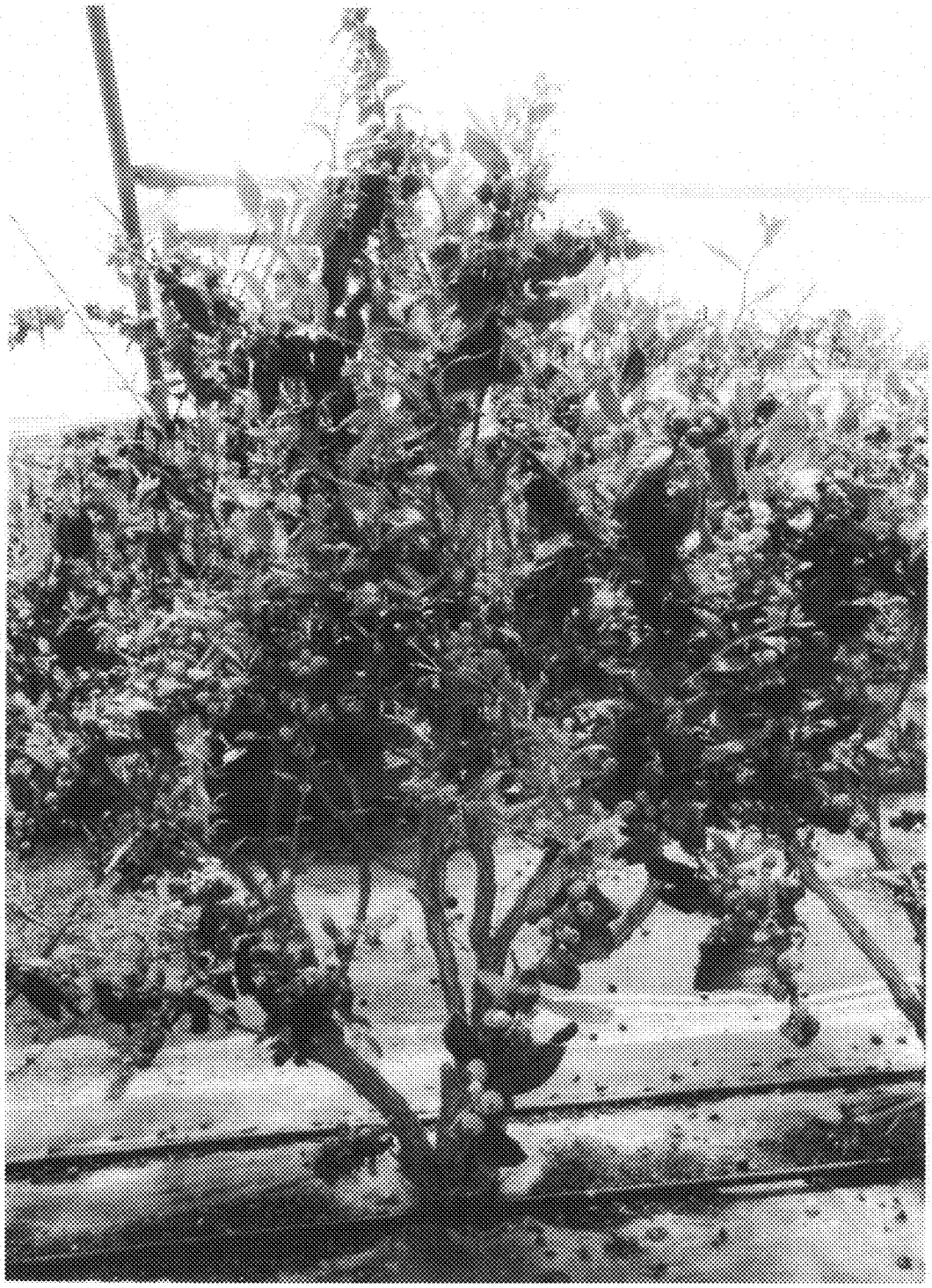
FIG. 2 shows an overall view of a typical fruiting plant of the new cultivar with berries in various stages of maturity.
Figure 3:
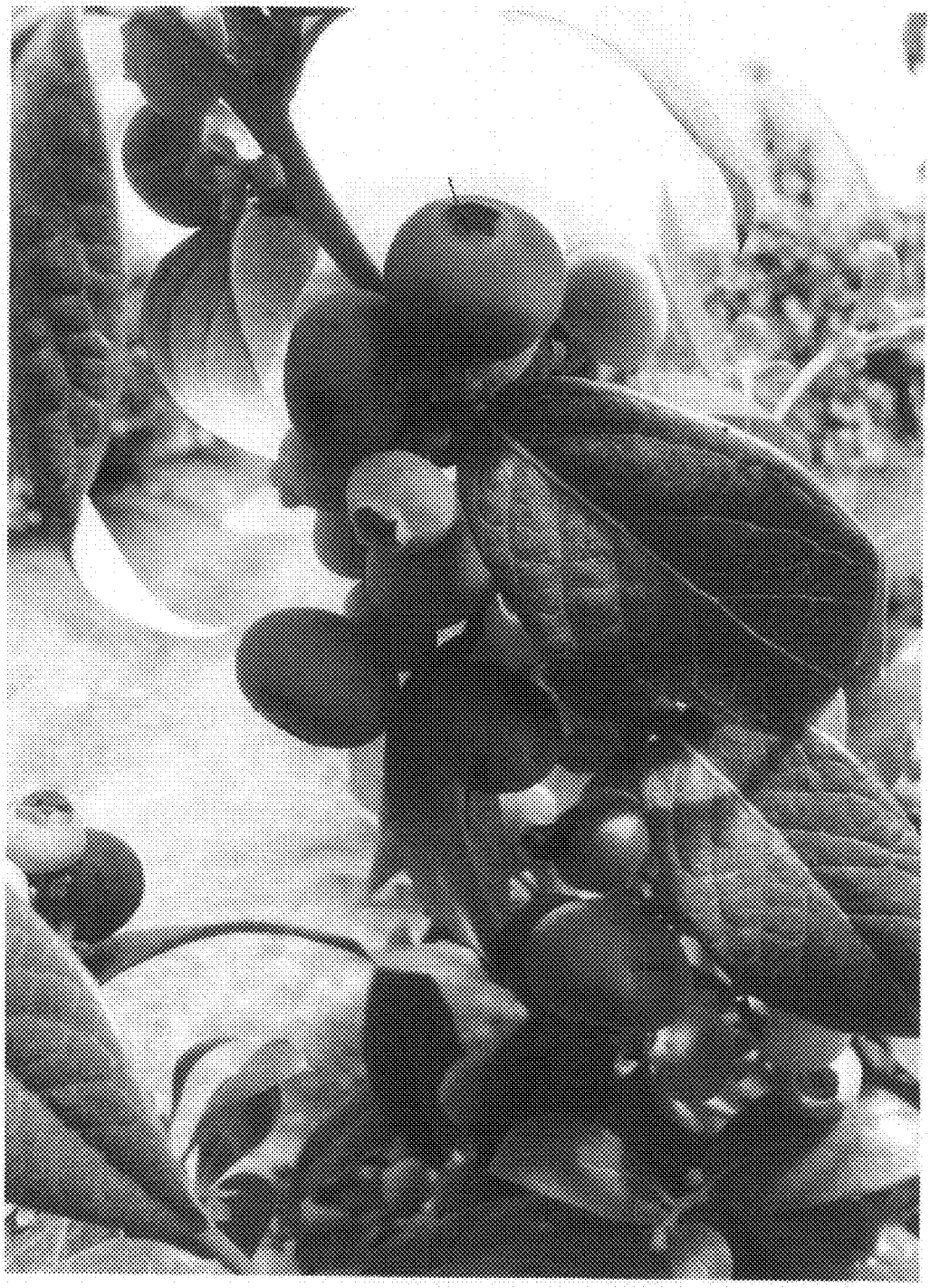
FIG. 3 shows a close view of typical berries of the new cultivar in various stages of maturity as well as typical foliage of the new cultivar.
Figure 4:
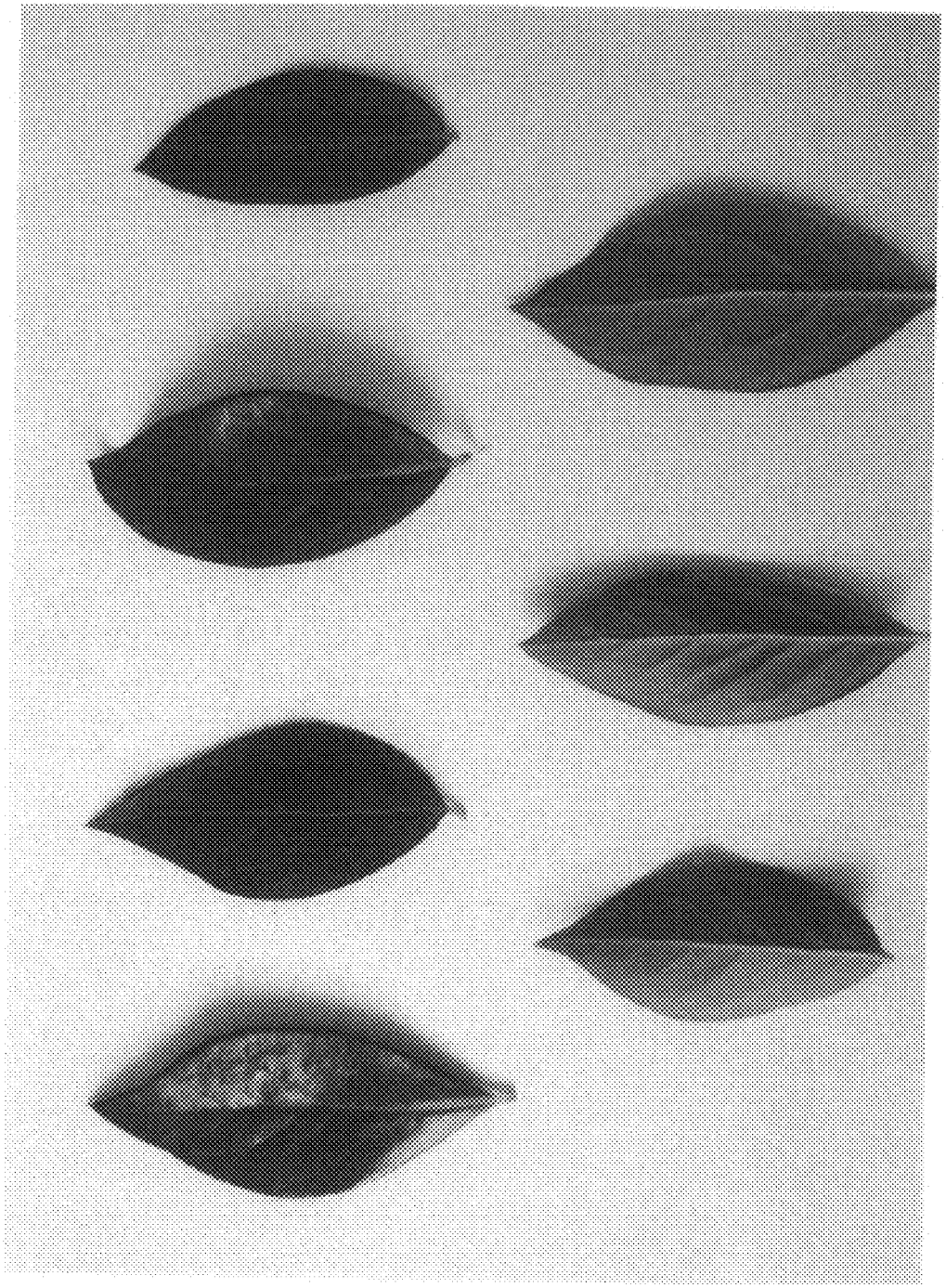
FIG. 4 shows the upper (adaxial) surfaces of typical leaves of the new cultivar at the top row, and under (abaxial) surfaces of typical leaves of the new cultivar at the bottom row.
Figure 5:
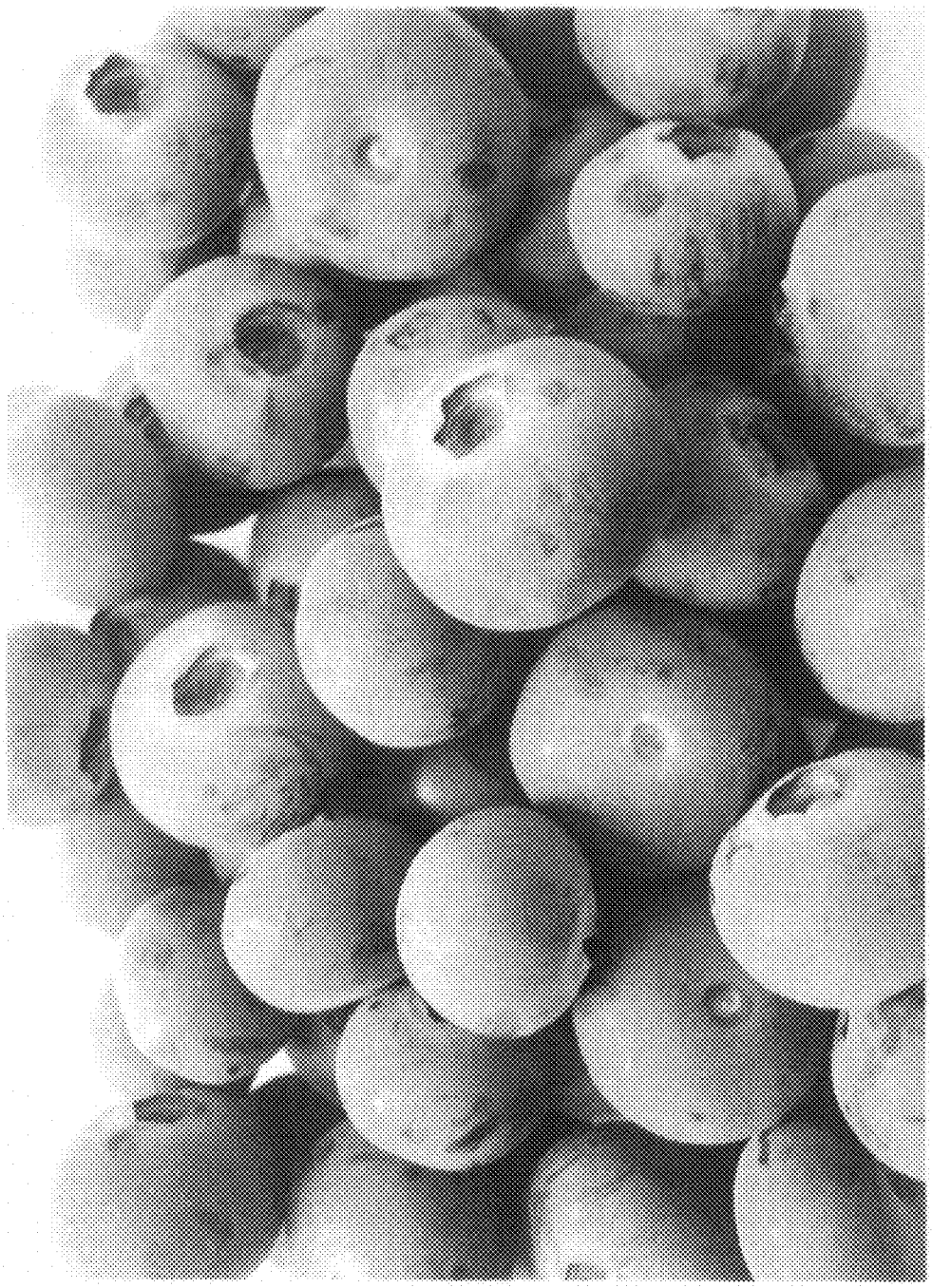
FIG. 5 shows an array of the mature dark blue berries of the new cultivar wherein a substantial bloom is apparent.
Figure 6:
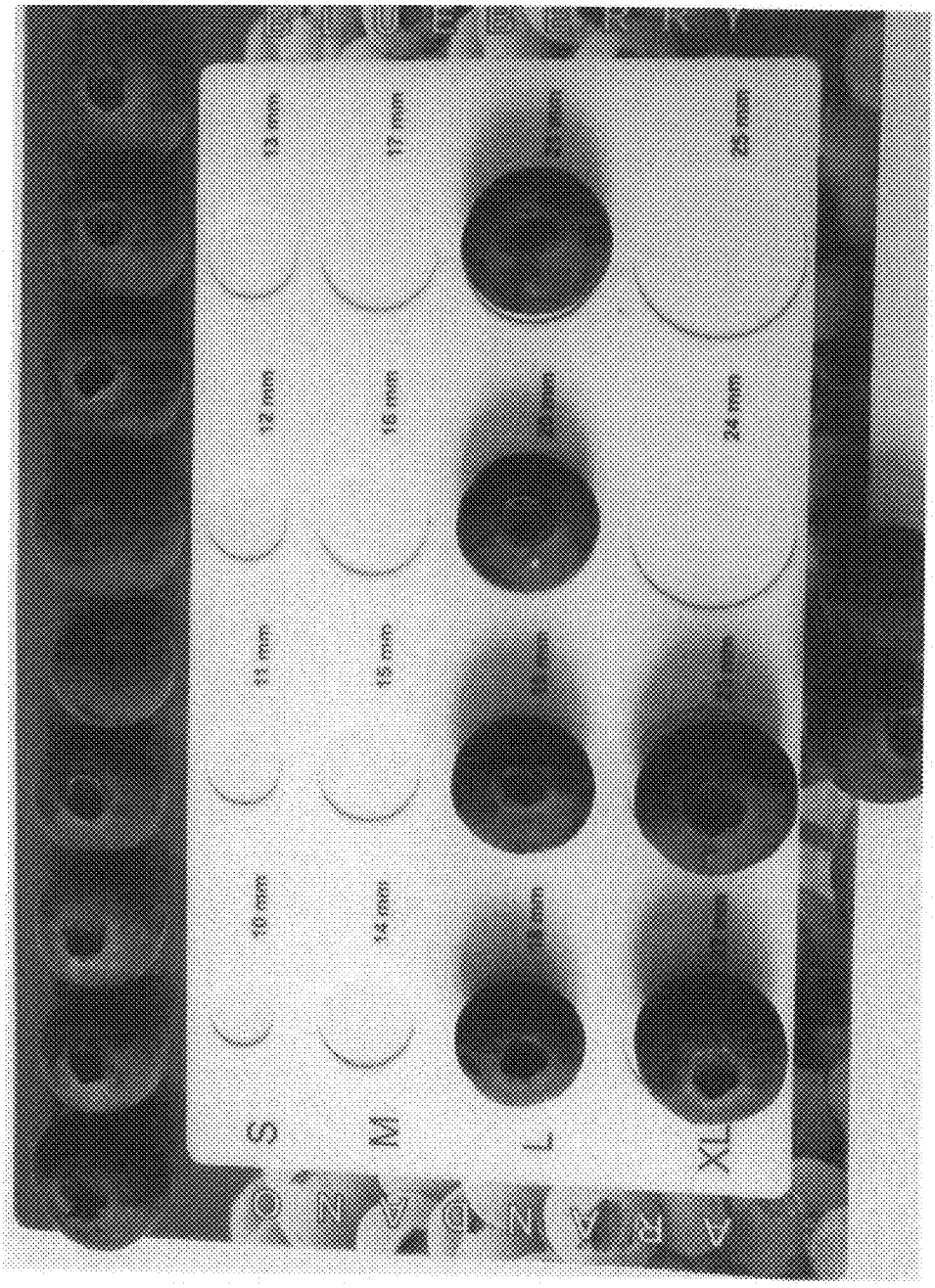
FIG. 6 shows a close view of the mature dark blue berries of the new cultivar together with a basis for size comparison.

The chart used in the identification of the colors described herein is the R.H.S. Colour Chart of The Royal Horticultural Society, London, England. Ordinary color terms are to be accorded their customary dictionary significance. The description is based on the observation while growing outdoors at Almonte, Huelva, Spain of approximately five-year-old plants of the new cultivar which had been asexually reproduced by the rooting of cuttings.

Plant:

*Growth habit.*—Generally round.

*Vigor.*—Medium.

*Height.*—Approximately 1.6 m at 5 years of age.

*Width.*—Approximately 3.5 m at 5 years of age.

*Trunk.*—Similar in appearance to that of the 'Sharpblue' cultivar with continually exfoliating vertical strips of bark and a smooth under surface, and commonly near Grey-Brown Group 199D in coloration.

*Branches.*—At five years of age commonly are approximately 42.8 cm in length on average, commonly possess a crotch angle of approximately 46.1° on average, commonly possess a cane coloration of near Yellow-Green Group 144B when less than about two years of age which changes to near Grey-Brown Group 199D with increasing age, and older canes commonly possess exfoliating bark similar to that present on the trunk.

*Foliage retention.*—Evergreen, with leaves being retained during the winter at Almonte, Huelva, Spain.

*Chill requirement.*—Less than 300 hours.

Foliage:

*Arrangement.*—Alternate.

*Shape.*—Narrowly elliptic.

*Length.*—Commonly approximately 49 mm on average.

*Width.*—Commonly approximately 27 mm on average.

*Apex.*—Acuminate.

*Base.*—Acute.

*Margin.*—Entire.

*Venation.*—A primary vein originates at the base and extends to the tip, sequences of pinnate lateral veins extend from the primary vein, and tertiary veins link the secondary veins to form a reticulate pattern.

*Texture.*—Pubescent and non-glandular.

*Color.*—Green Group 137B on the upper (adaxial) surface, and Green Group 138C on the under (abaxial) surface.

*Petiole.*—Commonly approximately 3.7 mm in length on average, approximately 0.7 mm in diameter on average, and near Yellow-Green Group N144D in coloration.

Flowers:

*Time.*—Early at Almonte, Huelva, Spain, with first flower commonly at approximately November 25$^{th}$, and 50 percent bloom at approximately February 1$^{st}$.

*Shape.*—Campanulate.

*Length.*—The corolla tube commonly is approximately 9.7 mm in length on average.

*Diameter.*—Commonly approximately 9.2 mm when open.

*Number.*—Commonly approximately 6 flowers per bud on average.

*Petals.*—5 in number and fused into a corolla tube.

*Petal size.*—Commonly approximately 9.7 mm in length on average and approximately 4.9 mm in width on average.

*Color.*—White Group 155C.

*Filaments.*—Commonly approximately 4.1 mm in length on average, commonly adnate in some flowers, pubescent, and pale green in coloration.

*Anthers.*—Bronze in coloration with a slightly darker pollen sack.

*Pistils.*—Bottle-shaped with narrowing towards the tip, approximately 1 mm in thickness on average towards the base, and light green in coloration.

*Styles.*—Approximately 8.7 mm in length on average.

*Pedicels.*—Approximately 7.4 mm in length on average, and near Yellow-Green Group N144A in coloration.

*Peduncles.*—Approximately 16.8 mm in length on average, and near Yellow-Green Group N144A in coloration.

*Fertility.*—Self-fertile, cross pollination is not required.

*Fragrance.*—None.

Fruit:

*Time.*—Early, commonly from approximately March 1$^{st}$ to May 21$^{st}$ at Almonte, Huelva, Spain (i.e., approximately 12 weeks).

*Shape.*—Generally flattened-round and somewhat pumpkin-shaped (as illustrated).

*Height.*—Commonly approximately 14 mm on average.

*Width.*—Commonly approximately 19 mm on average.

*Weight.*—Approximately 2.66 g/berry on average during 2007 when plants were 4 years of age.

*Fruit scar.*—Approximately 1.5 mm in size on average.

*Fruit scar tear.*—Substantially none.

*Seed number.*—Commonly approximately 10 per berry on average.

*Seed size.*—Commonly approximately 1.69 mm in length on average and approximately 1.19 mm in width on average.

*Immature color.*—Commonly near Green Group 142D with bloom and Yellow-Green Group 145A without bloom.

*Mature color.*—Light blue, Violet-Blue Group 98B with bloom and Black Group 202A without bloom.

*Flesh color.*—Internal flesh color of ripe berry is near White Group 155C.

*Productivity.*—Very abundant, approximately 3.6 Kg/plant on average during 2007 when plants were 4 years of age.

*Flavor.*—Excellent very sweet flavor.

Development:

*Ability to store.*—When stored at 20° C., approximately 77 percent of the harvest commonly is of good quality 7 days after harvest, and when stored at 8° C., approximately 88 percent of the harvest is of good quality 7 days after harvest.

*Disease tolerance.*—No special sensitivity to common Blueberry diseases, such as Leaf Rust (*Pucciniastrum vacinii*) and Botrytis Blight (*Botrytis cinerea*) has been encountered during observations to date at Almonte, Huelva, Spain.

*Insects.*—Is susceptible to aphids and thrips.

*Winter hardiness.*—Good, has withstood a temperature of −10° C.

*Heat tolerance.*—Good, has withstood a temperature as high as 45° C.

*Cultural conditions.*—Does well in well drained soils in a low-chilling area with more sandy soils or a particularly hot climate requiring more water.

*Market use.*—Primarily fresh fruit consumption.

Plants of the 'Dolores' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers early and forms fruit that ripens early, (b) displays a generally round growth habit with attractive evergreen foliage, (c) is self-fertile, (d) displays a low chilling requirement, and (e) forms in abundance attractive large dark blue crisp berries that exhibit a very sweet flavor;

substantially as herein shown and described.

* * * * *